United States Patent [19]

Tsuruoka et al.

[11] Patent Number: 5,312,833
[45] Date of Patent: May 17, 1994

[54] METHOD OF INHIBITING TUMOR GROWTH USING XANTHOCILLIN X DIMETHYLETHER

[75] Inventors: Tsutomu Tsuruoka; Harumi Fukuyasu; Katsumi Kawaharajo; Masao Koyama; Hiroshi Kurihara, all of Yokohama, Japan

[73] Assignee: Meiji Seika Kaisha, Ltd., Tokyo, Japan

[21] Appl. No.: 792,993

[22] Filed: Nov. 15, 1991

[30] Foreign Application Priority Data

Nov. 16, 1990 [JP] Japan .................................. 2-308843

[51] Int. Cl.$^5$ .......................................... A61K 31/275
[52] U.S. Cl. .................................................... 514/525
[58] Field of Search ......................................... 514/525

[56] References Cited

FOREIGN PATENT DOCUMENTS 0398336 11/1990 European Pat. Off. ............ 514/525

OTHER PUBLICATIONS

C. Takahashi et al., "The Structures of Toxic Metabolites of *Aspergillus candidus*. II. The Compound B (Xanthoascin), a Hepato- and Cardio-toxic Xanthocillin Analog" in Chem. and Pharma. Bul., vol. 24, No. 10, Oct. 1976, pp. 2317-2321.
N. Kitahara et al., "Xanthocillin X Monomethylether, a Potent Inhibitor of Prostaglandin biosynthesis" in Jour. of Antibiotics, vol. 34, No. 12, Dec. 1981, pp. 1556-1561.
K. Ando et al., "A New Antibiotic, 1-(p-hydroxyphenyl)-2,3-diisocyano-4-(p-methoxyphenyl)-buta-1,3-diene. I. Isolation and Biological Properties", Jour. of Antibiotics, vol. 21, No. 10, Oct. 1986, pp. 582-586.
A. Takatsuki et al., "New Antiviral Antibiotics: Xanthocillin X mono and Dimethylether and Methoxyxanthocillin X Dimethylether . . . ", Jour. of Antibiotics, vol. 21, No. 12, Dec. 1968, pp. 676-680.
The Merck Index, 10th Ed, Merck & Co., Inc., Rahway, N.J., 1983, pp. 1444-1445 No. 9873.

*Primary Examiner*—Jerome D. Goldberg
*Attorney, Agent, or Firm*—Varndell Legal Group

[57] ABSTRACT

Tumor growth in a mammal is inhibited by the administration of an effective amount of xanthocillin X dimethylether. The xanthocillin X dimethylether is administered in a range of 10-3,000 milligrams per day for an average adult human patient. The xanthocillin X dimethylether can be administered orally, by direct application into a neoplastic lesion, or by other parenteral forms of administration including intravenous, subcutaneous, or intramuscular injections. Also, suppository forms can be used.

9 Claims, No Drawings

METHOD OF INHIBITING TUMOR GROWTH USING XANTHOCILLIN X DIMETHYLETHER

FIELD OF THE INVENTION

The invention is concerned with inhibiting tumor growth. More specifically, the invention relates to methods of inhibiting tumor growth using xanthocillin X dimethylether.

BACKGROUND OF THE INVENTION

Malignant tumors are the primary cause of death among the Japanese and are a significant cause of death among other people of the world. To control this dreaded disease, remarkable progress has been made using various types of therapy encompassing chemotherapy, surgical therapy, and radiotherapy. Recently chemotherapy has begun to gain ground in the control of specific types of cancer, including leukemia among relatively young patients. For solid tumors, however, surgical treatment is considered first and is the treatment of choice in most instances. Only a very few patients having solid tumors recover with chemotherapy alone.

The potency of most chemotherapeutic agents is insufficient to suppress cellular proliferation of solid tumors. Furthermore, various adverse effects associated with these chemotherapeutic agents pose a significant limitation to the application of chemotherapy.

A class of chemotherapeutic agents of special interest is antibiotics. A number of U.S. patents are known which disclose antibiotics having antitumor effects. In this respect, the following U.S. patents are disclosed along with the respective antibiotic:

| Ohba | 4,994,578 | duocarmycin |
| --- | --- | --- |
| Saito et al. | 4,946,957 | DC-52 derivatives |
| Horton et al. | 4,870,058 | 14-acyloxy-2'-halo-anthracycline |
| Stefanska et al. | 4,824,944 | enamine derivatives of daunorubicin and adriamycin |
| Schmitz | 4,302,470 | acanthifolic acid |
| Pinnert et al. | 3,997,663 | daurorubicin and derivatives |

None of the above U.S. patents disclose the use of a xanthocillin to inhibit tumor growth.

SUMMARY OF THE INVENTION

The present invention is directed to the use of xanthocillin X dimethylether to inhibit tumor growth.

The formula for xanthocillin X dimethylether is as follows:

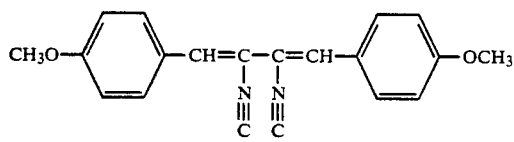

DETAILED DESCRIPTION OF THE INVENTION

The compound of the present invention is highly effective in the control of many tumors, especially solid tumors and yet has a low toxicity. Xanthocillin X dimethylether is a known substance produced by Dichotomomyces albus (N. Kitahara and A. Endo, J. Antibiotics, Vol. 34, No. 12, pages 1556–1561, December 1981 and Ando et al., J. Antibiotics, Vol. 21, No. 10, pages 582–586 (October 1968)). Xanthocillin X dimethylether has been isolated and purified as a specific inhibitor of prostaglandin synthesis.

Xanthocillin X dimethylether can be prepared by a number of methods. Xanthocillin X dimethylether is listed as a known compound in the Merck Index, 10th edition (1983), page 1444, in the entry for "Xanthocillin X." Xanthocillin X dimethylether can also be prepared by the following method.

13 mg of xanthocillin X monomethyl ether is dissolved in 2 ml of DMF and 40 mg of potassium carbonate is added thereto. Further, 50 μl of methyl bromide is added thereto and the mixture thus formed is extracted with 30 ml portions of ethyl acetate thrice. The extracts are combined, successively washed with water and a saturated aqueous solution of sodium chloride and dried over sodium sulfate. The sodium sulfate is filtered off, and the solvent is distilled from the filtrate. Thus, approximately 15 mg of xanthocillin X dimethylether is obtained in the form of a yellow solid.

The compound of the present invention can be used to inhibit growth of cancer cells in a mammal to which cells xanthocillin X dimethylether is cytotoxic. The compound of the present invention can be used as antineoplastic (anti-tumor) agent alone, for example, to inhibit tumor growth; or it may be combined with other known antineoplastic antibiotics, immunologically active antineoplastic agents, and antimetabolites.

The compound used in the present invention can be administered in many ways, including oral and parenteral administrations may be used. For parenteral administration, intravenous, subcutaneous, or intramuscular injections or suppository forms can be used. The compound can be administered by direct application to a neoplastic lesion, such as by injecting the compound in a pharmaceutically acceptable carrier in a region where neoplastic cells are present. Further enhancement of the antineoplastic potency of xanthocillin X dimethylether can be expected by direct application into the neoplastic lesion (cancer cells).

With respect to dosage, 100 to 3,000 mg/day (for adult humans or other mammals of similar body weight) can be given all at once or divided and given several times a day. The exact dosage is determined according to the sex, age, body weight, and symptoms of the patient, route of administration, and frequencies of administration.

The dosage forms for oral administration may be capsules, tablets, granules, fine particles, and powders. These preparations can be compounded with excipients such as starch, lactose, mannitol, ethylcellulose, and sodium carboxymethylcellulose. They can also be combined with lubricants such as magnesium stearate or calcium stearate.

For bonding agents, gelatin, gum arabic, cellulose ester, or polyvinylpyrrolidone can be used. For parenteral administration, aseptic aqueous or non-aqueous solution or emulsions can be used. For the carriers of non-aqueous solutions or suspensions, propylene glycol, polyethylene glycol, glycerin, olive oil, corn oil, and ethyl oleate can be used. For the carriers of suppositories, cacao butter or macrogeis can be used.

Preparation of a representative tablet made in accordance with the invention is described in Example 1.

EXAMPLE 1

| Xanthocillin X dimethylether | 60 mg |
| --- | --- |
| Lactose | 100 mg |
| Potato starch | 60 mg |
| Polyvinylpyrrolidone | 12 mg |
| Magnesium stearate | 3 mg |

Xanthocillin X dimethylether was pulverized, mixed with lactose and potato starch, and combined with an aqueous solution of polyvinylpyrrolidone. The mixture was uniformly mixed and moistened, and then put through a sieve with a 1 mm mesh, dried at 45° C., and again put through a sieve with a 1 mm mesh. The granules thus produced were thoroughly mixed with magnesium stearate and compressed into tablets.

A test for cytotoxic effects is presented in Example 2.

EXAMPLE 2

The effect of a preparation containing xanthocillin X dimethylether on cancer cells was determined by an in vitro test. For a medium, the Modified Dulbecco Minimum Essential Medium combined with 10% fetal serum was placed in a culture dish. The cytotoxic activity was observed on various cancer cells (set forth in Table 1 below) that were serially cultured in this medium in a $CO_2$ incubator. First, the respective cancer cells were suspended in the aforementioned culture medium at a concentration of $5 \times 10^4$ cells/ml. Then 135 μl of the suspension was added to a micro-titer plate having 96 wells. Next, 15 μl of the test compound solution was added, and the plates were incubated in $CO_2$ for 3 days. The survival of the cells after the incubation period was determined by the MTT assay (Igaku no Ayumi, Vol. 128, pages 733–735, 1984).

Table 1 shows $IC_{50}$ (drug concentration to kill 50% of the cells) of xanthocillin X dimethylether.

TABLE 1

| Cell Strain | $IC_{50}$ (μg/ml) |
| --- | --- |
| Meth-A | 0.71 |
| P388 | 0.67 |
| Lewis carcinoma of the lung | 0.46 |
| B16 | 0.45 |

As indicated in Table 1, xanthocillin X dimethylether was found to be cytotoxic to a series of cancer cells.

In Example 3, the activity of xanthocillin X dimethylether in suppressing the growth of a Meth-A solid tumor is discussed.

EXAMPLE 3

0.1 ml of $10^7$ cells/ml of murine fibrosarcoma Meth-A (ascites) were inoculated subcutaneously into Balb/c mice (6-week-old, females) and the test agent was injected intraperitoneally into the mice on the next day.

The test compound had been thoroughly pulverized in a mortar, suspended in 1% carboxymethylcellulose (CMC), and mixed well using ultrasonic. The test compound was administered once daily for 4 consecutive days. Following 2 weeks of rearing, the tumor on the back was excised and its weight was recorded. The percentage by which tumor development was suppressed was computed as follows: {(tumor weight of the control−tumor weight of the test group)/tumor weight of the control group} × 100.

Table 2 shows the percentage of tumor growth suppressed by xanthocillin X dimethylether.

TABLE 2

| Compound | Dosage/day[1] (mg/kg) | Tumor weight[2] (g) | Percentage suppression of tumor growth |
| --- | --- | --- | --- |
| xanthocillin X dimethylether | 30 | 0.11 ± 0.10 | 88.5 |
| control[3] | | 0.96 ± 0.60 | 0 |

[1] administered once daily for 4 consecutive days.
[2] mean ± standard deviation
[3] 1% CMC administered once daily for 4 consecutive days As shown in Table 2, xanthocillin X dimethylether markedly suppressed the growth of Meth-A solid tumors.

The acute toxicity of xanthocillin X dimethylether was investigated in Example 4.

EXAMPLE 4

Xanthocillin X dimethylether (by way of the same suspension as used in Example 3) was injected into the peritoneal cavity of Balb/c mice (7-week-old females). The animals were reared for the next 2 weeks and their survival was recorded.

Acute toxicity, $LD_{50}$, of xanthocillin X dimethylether was over 120 mg/kg.

As indicated above, the compound of the present invention is associated with low toxicity and yet possesses an extremely potent antiproliferative action against solid tumors that normally resist the actions of other neoplastic agents. Therefore, the compound can be used as an antineoplastic agent with a wide spectrum of applications.

What is claimed is:

1. A method of inhibiting growth of cancer cells in a mammal against which xanthocillin X dimethylether is effective comprising a step of administering to the mammal an effective amount of xanthocillin X dimethylether for inhibiting the growth of cancer cells against which the xanthocillin X dimethylether is effective.

2. The method of inhibiting growth of cancer cells as set forth in claim 1, wherein the xanthocillin X dimethylether is administered in a range of 100 to 3,000 milligrams per day for an average adult human patient.

3. The method of inhibiting growth of cancer cells as set forth in claim 1, wherein the xanthocillin X dimethylether is administered in a dose of approximately 30 milligrams per day per kilogram of mammal body weight.

4. The method of inhibiting growth of cancer cells as set forth in claim 1, wherein the xanthocillin X dimethylether is administered orally.

5. The method of inhibiting growth of cancer cells as set in claim 1, wherein the xanthocillin X dimethylether is administered parenterally.

6. The method of inhibiting growth of cancer cells as set forth in claim 1, wherein the xanthocillin X dimethylether is administered by direct application into the cancer cells.

7. The method of inhibiting growth of cancer cells as set forth in claim 1, wherein the cancer cells are a member selected from the group consisting of Meth-A, P388, Lewis carcinoma of lung and B16.

8. The method of inhibiting growth of cancer cells as set forth in claim 1, wherein the cancer cells are Meth-A.

9. The method of inhibiting growth of cancer cells as set forth in claim 1, wherein the growth of cancer cells is solid growth.

* * * * *